(12) United States Patent
Cerchiari et al.

(10) Patent No.: US 11,638,654 B2
(45) Date of Patent: May 2, 2023

(54) DETACHABLE AND RETRIEVABLE STENTS FOR THERAPEUTIC AGENT DELIVERY

(71) Applicant: COOK MEDICAL TECHNOLOGIES LLC, Bloomington, IN (US)

(72) Inventors: Alec E. Cerchiari, Bloomington, IN (US); Brian Feng, Bloomington, IN (US); Timothy Foley, Springville, IN (US); Christopher Mobley, Bloomington, IN (US); Gary Neff, Bloomington, IN (US); Ram H. Paul, Jr., Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 148 days.

(21) Appl. No.: 17/096,056

(22) Filed: Nov. 12, 2020

(65) Prior Publication Data
US 2021/0154031 A1 May 27, 2021

Related U.S. Application Data

(60) Provisional application No. 62/938,445, filed on Nov. 21, 2019.

(51) Int. Cl.
*A61F 2/95* (2013.01)
*A61F 2/88* (2006.01)

(52) U.S. Cl.
CPC ............ *A61F 2/95* (2013.01); *A61F 2/88* (2013.01); *A61F 2/9522* (2020.05); *A61F 2002/9511* (2013.01); *A61F 2002/9528* (2013.01)

(58) Field of Classification Search
CPC .......... A61F 2/95; A61F 2/9522; A61F 2/966; A61F 2002/9505; A61F 2002/825; A61F 2002/9528; A61F 2002/9511
See application file for complete search history.

(56) References Cited

U.S. PATENT DOCUMENTS

| | | | |
|---|---|---|---|
| 5,882,335 A * | 3/1999 | Leone | A61F 2/88 606/108 |
| 6,676,692 B2 | 1/2004 | Rabkin et al. | |
| 6,837,901 B2 | 1/2005 | Rabkin et al. | |
| 7,163,555 B2 | 1/2007 | Dinh | |

(Continued)

FOREIGN PATENT DOCUMENTS

WO WO2007/138608 6/2007

*Primary Examiner* — William H Matthews
(74) *Attorney, Agent, or Firm* — Crowell & Moring LLP (57) ABSTRACT

The present embodiments provide systems and methods for treating a medical condition. In one embodiment, the system comprises a stent having proximal and distal regions, and further having a delivery state and an expanded state. A therapeutic agent is disposed on a segment of the stent. The stent is disposed around an exterior surface of a core assembly in the delivery state. A coupling assembly releasably secures the proximal region of the stent to the exterior surface of the core assembly. The coupling assembly secures the stent to the core assembly for a predetermined period while the stent is in the expanded state and during release of the therapeutic agent at a target site. The coupling assembly further enables the stent to be disengaged from the core assembly and deployed in a bodily passageway.

19 Claims, 7 Drawing Sheets

(56) References Cited

U.S. PATENT DOCUMENTS

| | | |
|---|---|---|
| 7,169,170 B2 | 1/2007 | Widenhouse |
| 8,101,199 B2 | 1/2012 | Larrick et al. |
| 8,128,680 B2 | 3/2012 | Arnault De La Menardiere et al. |
| 8,157,855 B2 | 4/2012 | Eidenschink et al. |
| 8,197,529 B2 | 6/2012 | Cully et al. |
| 8,540,761 B2 | 9/2013 | Rabkin et al. |
| 9,192,500 B1 | 11/2015 | Longo et al. |
| 9,795,772 B2 | 10/2017 | Aggerholm et al. |
| 9,808,359 B2 | 11/2017 | Ferrera et al. |
| 9,884,142 B2 | 2/2018 | Bureau et al. |
| 2005/0131523 A1 | 6/2005 | Bashiri et al. |
| 2008/0097580 A1 | 4/2008 | Dave |
| 2011/0106234 A1 | 5/2011 | Grandt |
| 2015/0073526 A1 | 3/2015 | Kluck |
| 2016/0374800 A1 | 12/2016 | You et al. |

\* cited by examiner

DETACHABLE AND RETRIEVABLE STENTS FOR THERAPEUTIC AGENT DELIVERY

PRIORITY CLAIM

This invention claims the benefit of priority of U.S. Provisional Application Ser. No. 62/938,445, entitled "Detachable and Retrievable Stents for Therapeutic Agent Delivery," filed Nov. 21, 2019, the disclosure of which is hereby incorporated by reference in its entirety.

BACKGROUND

The present embodiments relate generally to medical devices, and more particularly, to therapeutic agent delivery stents having detachable and/or retrievable features.

Vascular therapy can encompass many medical treatments to the vascular system. One example is the general systemic administration of a therapeutic agent within a body vessel. Although many medical conditions are satisfactorily treated by the general systemic administration of the therapeutic agent, the treatment of many conditions require delivery of the therapeutic agent locally within a body vessel. More specifically, delivery of the therapeutic agent is to only a selected portion of internal body tissue, without delivering the therapeutic agent to surrounding tissue or requiring additional systemic delivery of the therapeutic agent. A systemically administered therapeutic agent may be absorbed not only by the tissues at the target site, but by other areas of the body. As such, one drawback associated with the systemic administration of therapeutic agents is that areas of the body not needing treatment are also affected.

Medical delivery catheters provide a minimally invasive means for delivering therapeutic agents to internal body tissue. To provide site-specific localized treatment, balloon catheters may be used to deliver the therapeutic agent exclusively to the target site within a body vessel. One example of a condition that is beneficially treated by local administration of the therapeutic agent with a balloon catheter is the delivery of the therapeutic agent in combination with percutaneous transluminal angioplasty (PTA). PTA is a technique used to dilate stenotic portions of blood vessels. During PTA, a catheter balloon is positioned at a blocked lumen or target site, and the balloon is inflated to cause dilation of the lumen. The balloon is deflated and the catheter is then removed from the target site and from the patient's lumen thereby to allow blood to flow freely through the unrestricted lumen.

During such procedures, some balloon catheters may occlude or block blood flow distal to the treatment site. Some perfusion balloon catheters only allow a small percentage of perfusion. Thus, there is often a time constraint imposed during the delivery of therapeutic agents in such localized manner, to ensure that blood flow is not significantly deprived downstream of the treatment site. Such time constraints may prevent delivery of the therapeutic agent for a desired duration, or may require a secondary procedure if the initial effort could not sufficiently delivery the agent.

Accordingly, it would be beneficial to provide a medical device for delivering a therapeutic agent locally within a body vessel, while allowing fluid flow to areas distal to the treatment site. Further, it is desirable to provide an operator with an option to remove the medical device after satisfactory delivery of the therapeutic agent, or to detach a portion of the medical device within the body for longer-term conditions.

SUMMARY

The present embodiments provide systems and methods for treating a medical condition. In one embodiment, a system comprises a stent having proximal and distal regions, and further having a delivery state and an expanded state. A therapeutic agent is disposed on a segment of the stent. The stent is disposed around an exterior surface of a core assembly in the delivery state. A coupling assembly releasably secures the proximal region of the stent to the exterior surface of the core assembly. The coupling assembly secures the stent to the core assembly for a predetermined period while the stent is in the expanded state and during release of the therapeutic agent at a target site. The coupling assembly further enables the stent to be disengaged from the core assembly and deployed in a bodily passageway.

In one embodiment, the stent comprises a proximal taper, a distal taper, and a central region extending therebetween. The stent may further comprise a plurality of members extending axially with a plurality of slots disposed between the plurality of members, wherein the plurality of slots permit perfusion distal to a treatment site when the stem is in the expanded state.

In one embodiment, the coupling assembly enables recapture of the stent after deployment inside of the bodily passageway. In one example, the coupling assembly comprises a coiled portion extending from the proximal region of the stent, and further comprises a retaining portion disposed on the core assembly. In this example, the coiled portion selectively interlocks with the retaining portion. In another example, the coupling assembly comprises a first retainer segment extending from the proximal region of the stent, a second retainer segment extending distally from a control member, and a protrusion of the first retainer segment that nests within a notch of the second retainer segment in a delivery state.

In an exemplary method for treating a medical condition, a stent is provided having proximal and distal regions, and further having a delivery state and an expanded state. A therapeutic agent is disposed on a segment of the stent. The stent is delivered to a target site while disposed around an exterior surface of a core assembly. A coupling assembly releasably secures the proximal region of the stent to the exterior surface of the core assembly during delivery. The stent is expanded to the expanded state, wherein the coupling assembly secures the stent to the core assembly for a predetermined period while the stent is in the expanded state and during release of the therapeutic agent at a target site. The coupling assembly may be actuated to disengage the stent from the core assembly to deploy the stent in a bodily passageway.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 10A-110B are side views depicting a further alternative coupling assembly in coupled and uncoupled states, respectively.

DETAILED DESCRIPTION OF THE PREFERRED EMBODIMENTS

In the present application, the term "proximal" refers to a direction that is generally closest to an operator during a medical procedure, while the term "distal" refers to a direction that is further from an operator during a medical procedure.

The present embodiments provide systems and methods for applying vascular therapy locally within a body vessel. A stent of the system can expand in order to have a portion positioned adjacent to a body vessel wall during therapeutic agent delivery, while simultaneously providing adequate interstices in another portion to allow fluid flow and perfusion to areas distal of the treatment site. Advantageously, such technique will not block fluid flow for an extended period of time to organs, such as the brain, heart or kidneys, while waiting for the therapy to be complete; for example, to allow the therapeutic agent to diffuse into the target tissue. As another advantage, the present systems and methods provide for an option to retain the stent against a core assembly during the stage of therapeutic agent delivery, and optionally to detach the stent from the core assembly, or to retrieve the stent after an initial deployment inside the body.

Figure 1:
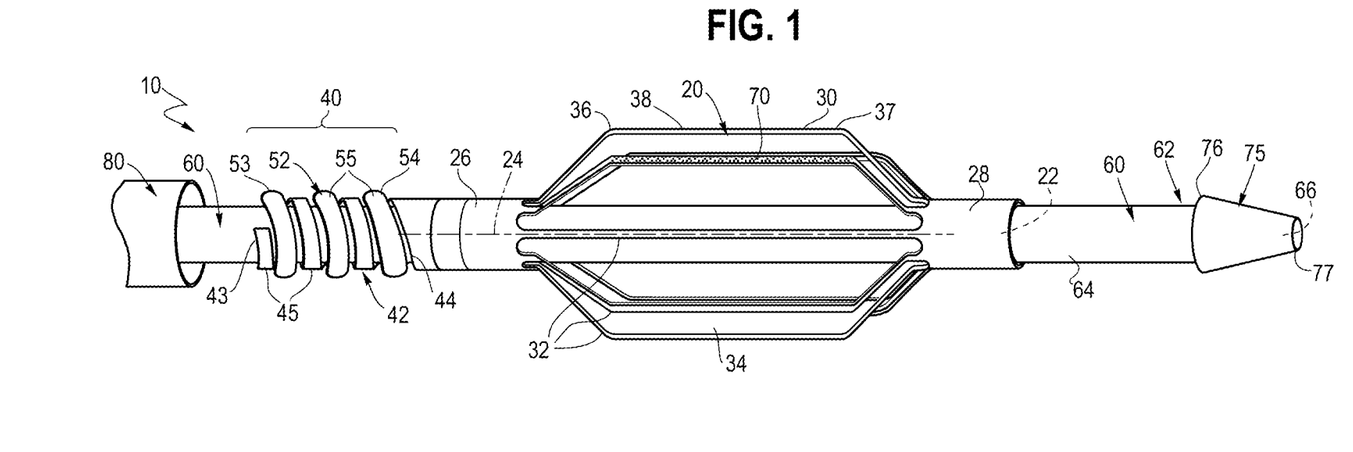
FIG. 1 is a side view of a first embodiment of a system for applying vascular therapy locally within a body vessel, with a stent in an expanded state.

Referring now to FIG. 1, a first embodiment of a system 10 for applying vascular therapy locally within a body vessel is shown and described. The system 10 comprises a stent 20, a coupling assembly 40, and a core assembly 60. A therapeutic agent 70 is disposed on at least a segment of the stent 20. As will be explained in further detail below, the coupling assembly 40 releasably secures a proximal region 26 of the stent 20 to an exterior surface 64 of the core assembly 60. The coupling assembly 40 enables the stent 20 to remain secured to the core assembly 60 for a predetermined period during release of the therapeutic agent 70 in a bodily passageway, and the coupling assembly 40 further enables the stent 20 to be disengaged from the core assembly 60 for deployment inside of the bodily passageway.

The core assembly 60 has a distal region 62, a proximal region (not shown) extending outside of a patient that may be manipulated by an operator, and a lumen 66 extending therebetween. The lumen 66 may receive a guidewire 79 (shown in FIGS. 5-6 below) or other components. In a delivery state, the stent 20 is disposed around the exterior surface 64 of the core assembly 60, as depicted in FIG. 1.

A sheath 80 is disposed radially outward of the core assembly 60, as shown in FIG. 1. The sheath 80 can protect the stent 20 during delivery and/or maintain the stent 20 in a compressed configuration during delivery.

An atraumatic tip 75 may be disposed at the distal region 62 of the core assembly 60. The atraumatic tip 75 comprises a proximal end 76 having an outer diameter greater than a distal end 77, as depicted in FIG. 1. In the delivery state, the sheath 80 may be disposed over both the stent 20 and the core assembly 60 such that the sheath 80 distally abuts the proximal end 76 of the atraumatic tip 75, thereby providing a substantially flush exterior surface to the overall system 10 suitable for percutaneous delivery.

Figure 2:
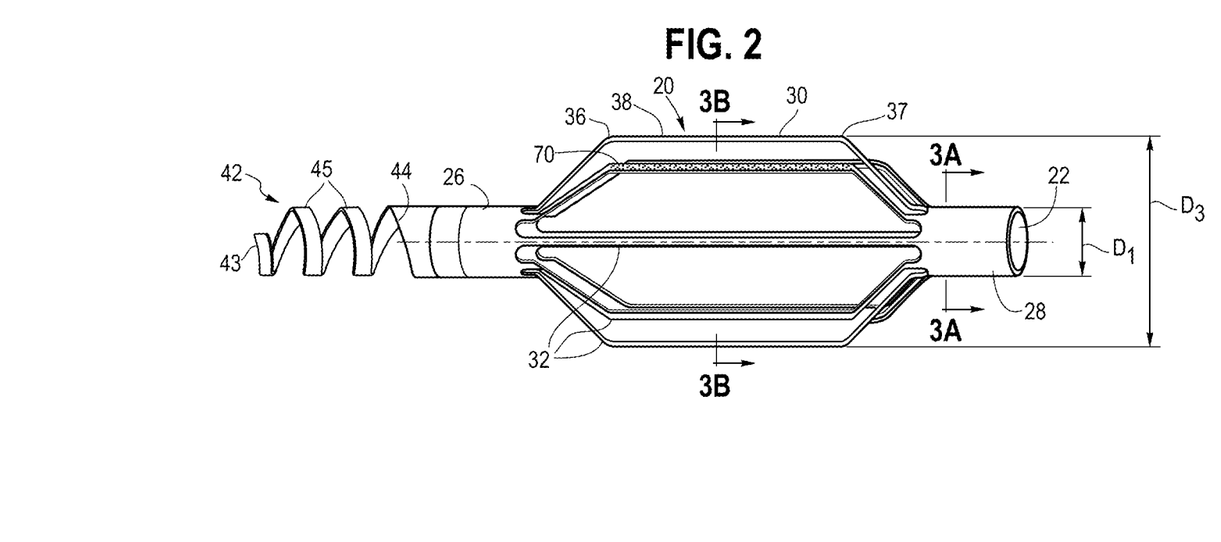
FIG. 2 is a side view of the stent of FIG. 1 in an isolated manner in the expanded state.
Figure 3A:
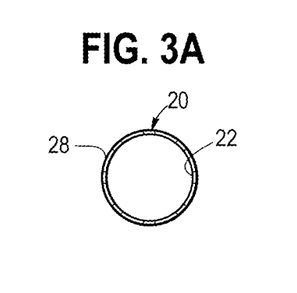
FIG. 3A is a cross-sectional view taken along line 3A-3A of FIG. 2.
Figure 3B:
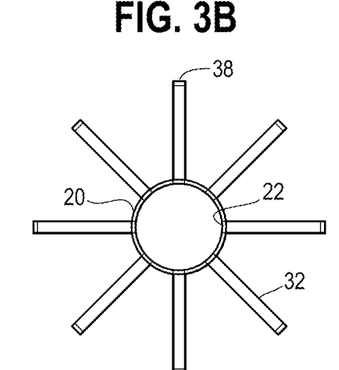
FIG. 3B is a cross-sectional view taken along line 3B-3B of FIG. 2.
Figure 3C:
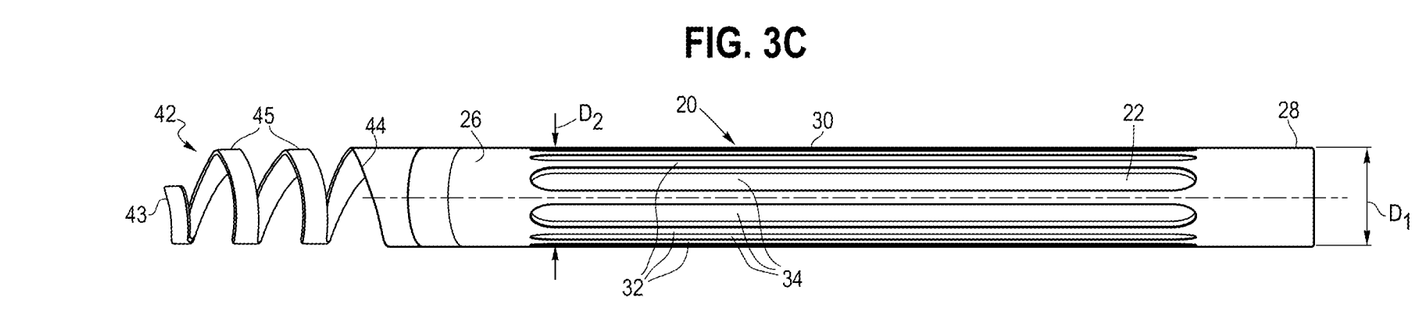
FIG. 3C is a side view of the stent of FIG. 1 in an isolated manner in a collapsed state.

Referring to FIGS. 2-3C, further features of the stent 20 are shown in an isolated manner, i.e., separated from the core assembly 60, for illustrative purposes. The stent 20 comprises a generally tubular frame having a lumen 22 about a longitudinal axis 24. The stent 20 has proximal and distal regions 26 and 28, and a central region 30 disposed therebetween.

As depicted in FIG. 2, the stent 20 can have a first diameter D1, which may be substantially the same at the proximal region 26 and the distal region 28 in both the expanded configuration and the compressed configuration. However, in other embodiments, the diameter of proximal region 26 and the distal region 28 of the stent 20 may be different. Notably, FIG. 3A is a cross-sectional view taken along line 3A-3A in FIG. 2 depicting a section of the stent 20 at the distal region 28.

Figure 6:
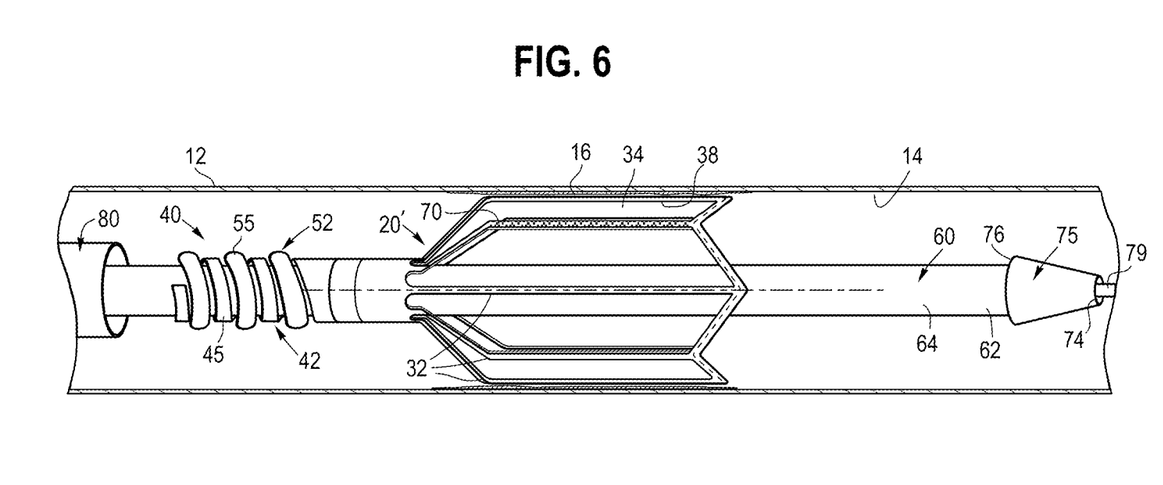
Figure 7:
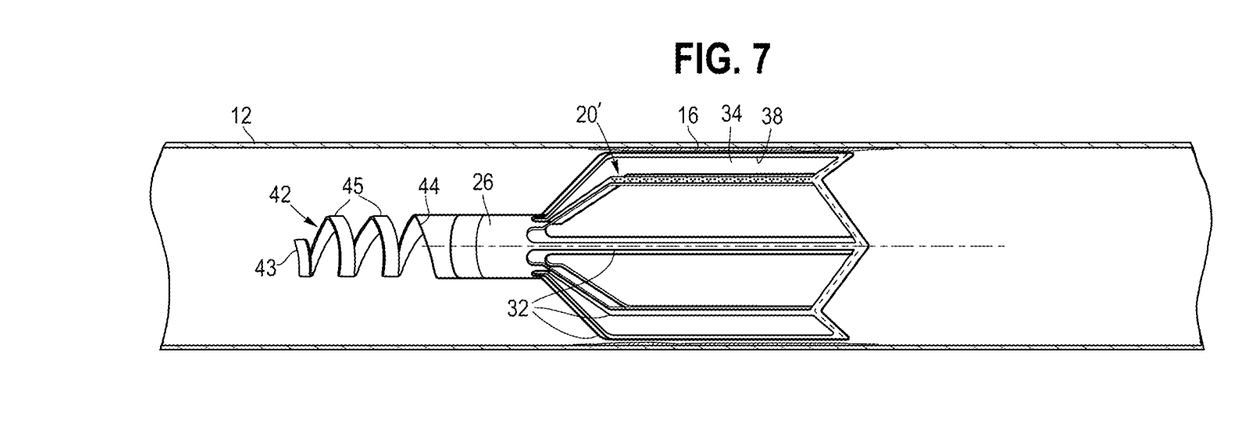
Figure 8:
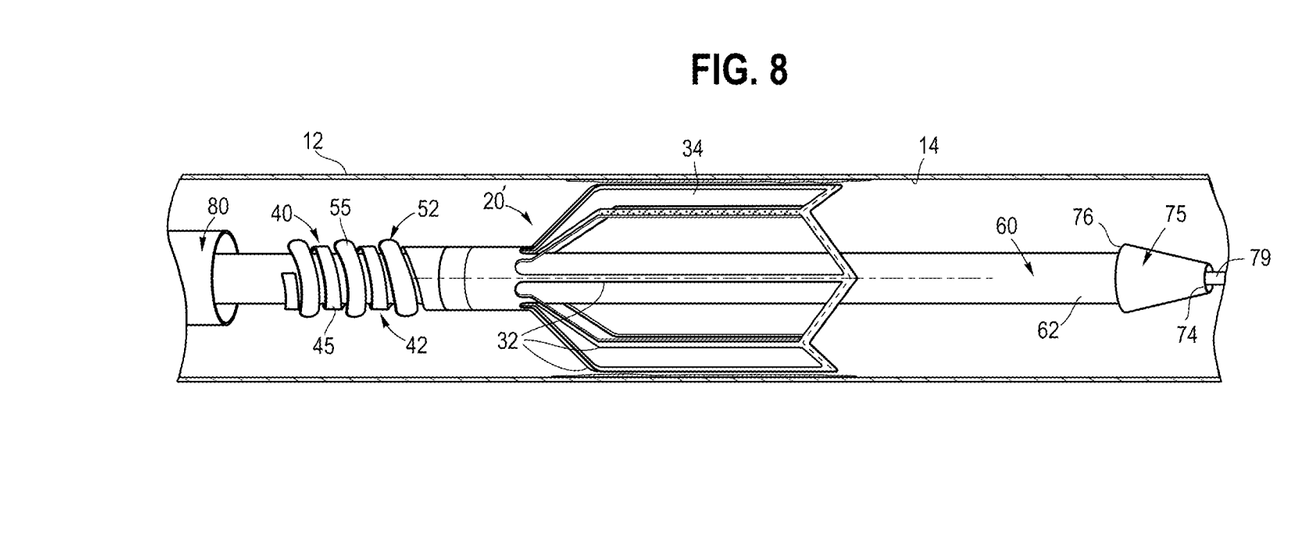

As seen in FIG. 2 and FIG. 3C, the central region 30 of the stent 20 includes a plurality of members 32. The members 32 define a series of slots 34 in between adjacent members 32. The series of slots 34 can be oriented substantially parallel to one another, circumferentially spaced equally around the central region 30, or both. The diameter of the central region 30 of the stent 20 can be different depending on whether the stent 20 is in the compressed configuration or in the expanded configuration. That is, the central region 30 can have a first diameter, noted as D2 in FIG. 3C, in the compressed configuration and a second diameter, noted as D3 in FIG. 2, in the expanded configuration. The second diameter D3 is preferably sized to fit within a body vessel 12 as shown in FIGS. 6-8 below.

FIG. 3B is a cross-sectional view taken along line 3B-3B in FIG. 2 depicting the members 32 in an expanded state. The second diameter D3 of the central region 30 is greater than the first diameter D2 of the central region 30. Preferably, the first diameter D2 of central region 30 is the same or substantially the same as the diameter D1 of the stent 20. However, the diameter D2 of central region 30 may be different than the first diameter D1 of the stent 20. In that case, the first diameter D2 of the central region 30 may be less than or greater than the first diameter D1 of the stent 20. In one example, the diameters D1, D2 are about 1 mm, and D3 can be about 4, 5, or 6 mm. The size of diameter D3 may also be about 4 mm to about 20 mm or more depending on the size of the body vessel, while diameters D1, D2 may be about 1 mm to about 5 mm. Although the figures illustrate the stent 20 having a middle region that is substantially cylindrical, the central region 30 may be suitably tapered to better match the shape of the body vessel.

The members 32 may be configured to be substantially straight and/or flat or in immediate contiguous proximity to each other without a substantial bent portion in the compressed configuration in order to make a more uniform profile during delivery, as shown in FIG. 3C. In FIG. 2, in the expanded configuration, the members 32 can have two vertices or bent portions 36 and 37, and a contacting portion 38 in between the vertices 36 and 37, where the contacting portion 38 can contact with the body vessel 12. Portions between the bent portions 36 and 37 and the respective proximal and distal regions 26 and 28 are suitably angled in order to form the contacting portions 38 and the interstices 40 when in the expanded configuration. The contacting portion 38 of the members 32 is configured to to substantially align with the body vessel 12 while the stent 20 is in the expanded configuration. Accordingly, the members 32 and the contacting portion 38 can have a cylindrical shape or can be suitably tapered to match the tapering of a body vessel. The number of members 32 can vary from 2 to 10 or more depending on the desired support for the body vessel.

The stent 20 may be manufactured from a super-elastic material. Solely by way of example, the super-elastic material may comprise a shape-memory alloy, such as a nickel titanium alloy (nitinol), If the stent 20 comprises a self-expanding material such as nitinol, the stent may be heat-set into the desired expanded state, whereby the stent 20 can assume a relaxed configuration in which it assumes the preconfigured first expanded inner diameter upon application of a certain cold or hot medium. Alternatively, the stent 20 may be made from other metals and alloys that allow the stent 20 to return to its original, expanded configuration upon deployment, without inducing a permanent strain on the material due to compression. Solely by way of example, the stent 20 may comprise other materials such as stainless steel, cobalt-chrome alloys, amorphous metals, tantalum, platinum, gold and titanium. The stent 20 also may be made from non-metallic materials, such as thermoplastics and other polymers.

Alternatively, the stent 20 can be designed to be expanded by mechanical means (i.e., the frames are not self-expanding). For example, the frame may be manufactured from an inert, biocompatible material with high corrosion resistance that can be plastically deformed at low-moderate stress levels, such as tantalum. The frames can be deployed by both assisted (mechanical) expansion and self-expansion means. In embodiments where the frame is deployed by mechanical expansion, the frame can be made from materials that can be plastically deformed. One widely used material for expandable structures is stainless steel, Alternative materials for mechanically expandable structural frames that maintain similar characteristics to stainless steel include tantalum, platinum alloys, niobium alloys, and cobalt alloys.

In another embodiment, the system 10 may further include a means for translating the distal region 28 of the stent 20 along the longitudinal axis 24 relative to the proximal region 26. This translation can move the stent 20 from the compressed configuration to the expanded configuration. One embodiment may include a free-standing distal region 28 and a fixed proximal region 26. The distal region 28 can be tied to a string, wire, or the like. The distal region 28 may then pulled by the string toward the proximal region 26, which can cause the members 32 to displace radially outward from the longitudinal axis 24. In another embodiment, the proximal region 26 may be free standing and the distal region 28 may be fixed. In this instance, a pusher sheath surrounding a catheter and adapted to engage the stent may be forced to translate distally the distal region 28, which may cause the members 32 to displace radially outward from the longitudinal axis 24. Yet, in another embodiment, both proximal region 26 and distal region 28 may be free standing. Here, the string, as described above, may be pulled to urge the distal region 28 toward the proximal region 26, and the pusher sheath around the catheter, as described above, may urge the proximal region 26 toward the distal region 28. With both actions, the members 32 can be displaced radially outward from the longitudinal axis 24.

The stent 20 may be fabricated using any suitable method known in the art. In one example, the complete frame structure is cut from a solid tube, or cannula, or sheet of material, and thus the frame would be considered a monolithic unit. The cannula may have a circular, elliptical, or similar like cross-section. Laser cutting, water-jet cutting and photochemical etching are all methods that can be employed to form the structural frame from sheet and tube stock. The series of slots are cut between the distal portion and the proximal portion, or in the middle region of the cannula, and extend radially through the cannula from the outer surface to interior surface. However, in other methods, the frame of the stent 20 can be fabricated by using two separate cannulas at the proximal and distal regions 26 and 28, and a series of intermediate struts that are then secured to the smaller sized cannulas. Still other methods for fabricating the complete frame structure as previously disclosed would be understood by one of ordinary skill in the art.

Referring still to FIGS. 1-3C, in this embodiment, the coupling assembly 40 comprises a coiled portion 42 extending from the proximal region 26 of the stent 20, and further comprises a retaining portion 52 disposed on the core assembly 60. As best seen in FIG. 2, the coiled portion 42 comprises a proximal end 43, a distal end 44 that extends from the proximal region of the stent 20, and a plurality of helical turns 45 disposed between the proximal and distal ends 43 and 44.

The coiled portion 42 of the coupling assembly 40 may be formed integrally with the remainder of the stent 20. For example, if the stent 20 is formed using a laser cannula cutting technique described above, the coiled portion 42 may be integrally formed by the laser, such to that the coiled portion 42 originates from the same material as the stent 20. Alternatively, the coiled portion 42 may be formed externally and its distal end 44 may then be secured to the proximal region 26 of the stent 20, e.g., using a solder, weld, adhesive, mechanical coupling, friction fit, or the like.

The retaining portion 52 of the coupling assembly 40 may be formed integrally or externally relative to the core assembly 60. In the example of FIG. 1, the retaining portion 52 comprises proximal and distal regions 53 and 54 disposed along a portion of the core assembly 60, and a plurality of helical turns 55 disposed between the proximal and distal regions 53 and 54. In one embodiment, the plurality of helical turns 55 may be molded into an exterior surface 64 of the core assembly 60, such that upraised helical peaks with valleys therebetween are on the exterior surface 64. In another embodiment, the core assembly 60 may comprises two distinct tubes separated by the helical turns 55, where the proximal region 53 is secured to a proximal tube and the distal region 54 is secured to a distal tube, thereby effectively forming a continuous, elongated core assembly 60.

As will be described further below with respect to FIGS. 5-8, the coiled portion 42 of the coupling assembly 40 may be selectively engaged to the retaining portion 52, thereby effectively securing the stent 20 to the core assembly 60. However, when the core assembly 60 and the stent 20 are rotated with respect to one another, the coiled portion 42 may disengage from the retaining portion 52, thereby releasing the stent 20 from the core assembly 60.

Referring still to FIGS. 1-3C, in a presently preferred embodiment, the stent 20 is used to deliver a therapeutic agent 70, which can be any anti-restenosis drug, gene regulatory compound, anti-thrombotic, or other bioactive agents. The therapeutic agent 70 may include an antithrombogenic bioactive agent. The antithrombogenic bioactive agent may include any therapeutic agent that inhibits or prevents thrombus formation within a body vessel. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa thromboxane A2, ADP-induced glycoprotein IIb/IIIa and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenala-nyl-L-poly-L-arginyl, chioromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

In some examples, the therapeutic agent 70 may deliver comprise an anti-restenotic drug such as paclitaxel or Limus drugs. The Limus drug may be, for example, sirolimus, pimecrolimus, tacrolimus, everolimus, zotarolimus, novolimus, myolinius, temsirolimus, deforolimus or biolimus It will be appreciated that while selected therapeutic agents 70 have been described, various additional or alternative therapeutic agents may be delivered by the stent 20 without departing from the scope of the present embodiments.

Application of the therapeutic agent 70 to the wall 14 of the body vessel 12 can occur by any means known in the art. The therapeutic agent 70 can be applied to the treatment site when the central region 30 of the stent 20 presses against the wall 14 of the body vessel 12. The therapeutic agent 70, however, can be applied based on the degradation of a coating on the agent at some time after the stent 20 presses against the wall 14 of the body vessel 12. Depending on the condition of the patient or subject, the agent applied will be specific for such condition, i.e., the concentration, potency, or both, may be limited only to the immediate site of treatment, to other areas surrounding the site of treatment, or both. Different therapeutic agents can be applied to the portion of the stent 20 contacting the body vessel to wall 14 to promote blood clotting or other therapy between the stent 20 and the body vessel wall 14.

Figure 4:
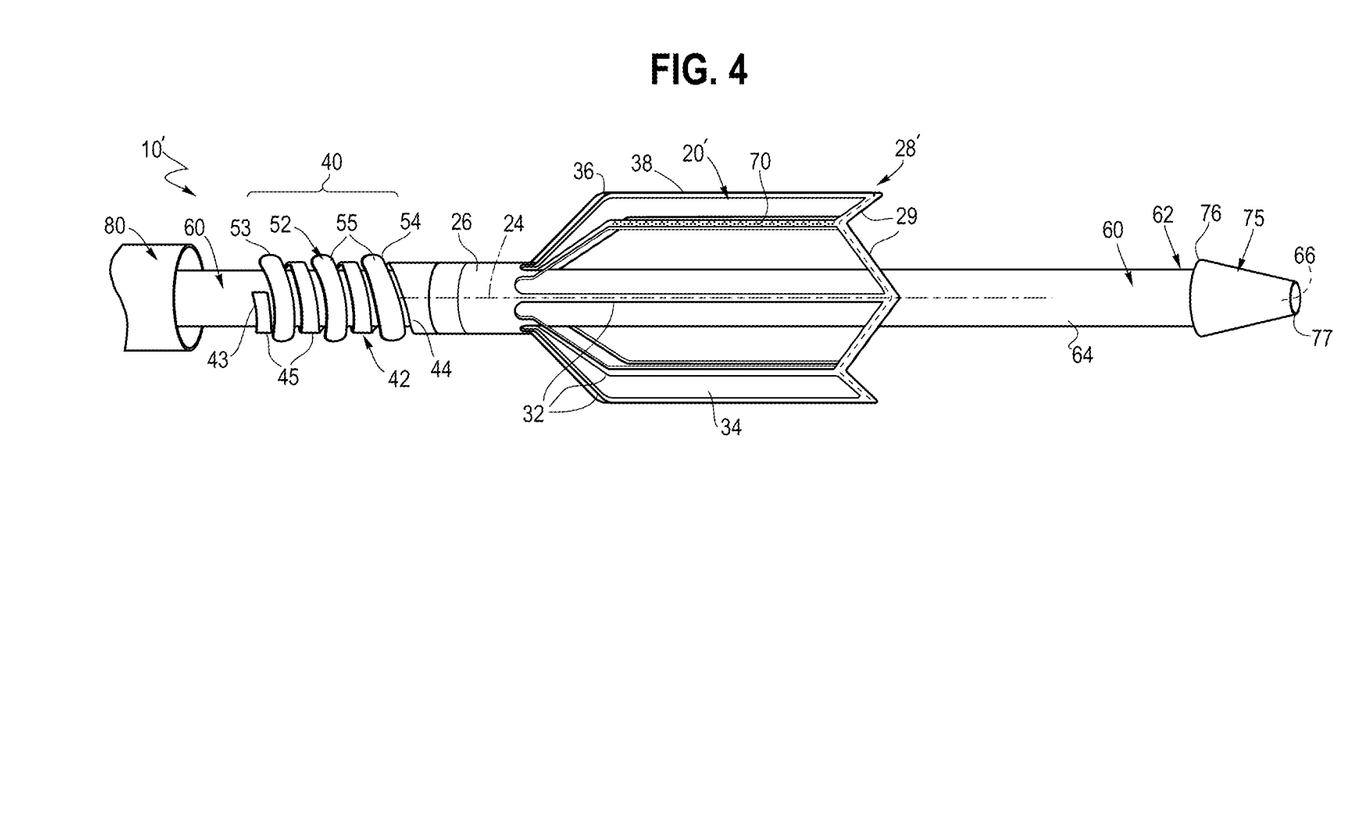
FIG. 4 is a side view of a second embodiment of a system for applying vascular therapy locally within a body vessel, with a stent in an expanded state.

Referring now to FIG. 4, a second embodiment of a system 10' for applying vascular therapy locally within a body vessel is shown and described. The system 10' comprises similar components to the system 10 of FIGS. 1-3C, with like reference numerals designating corresponding parts and notable exceptions described below. In particular, the system 10' comprises an alternative stent 20', which differs from the stem 20 in that the stent 20' has an expandable distal region 28'. Thus, during a procedure, e.g., upon initial proximal retraction of the sheath 80, the distal region 28' may flare out to an increased diameter, e.g., which may be about the same as the contacting portion 38, as depicted in FIG. 4. Optionally, one or more connecting struts 29 may be disposed between adjacent member 32 near the distal region 28', as depicted in FIG. 4, to provide structural support without interfering with expansion of the stent 20'. As described further below, the stent 20' may be advantageous in situations when the delivery system is removed during a procedure, so the delivery system may be more readily withdrawn.

Referring now to FIGS. 5-8, exemplary method steps for using the system 10 or system 10' of FIGS. 1-4 in the body vessel 12 are shown and described. For the sake of brevity, the discussion related to FIGS. 5-8 may describe use of the system 10' and stent 20', but it will be appreciated that the same steps may apply during operation of the system 10 and stent 20 due to the commonality of components.

Figure 5:
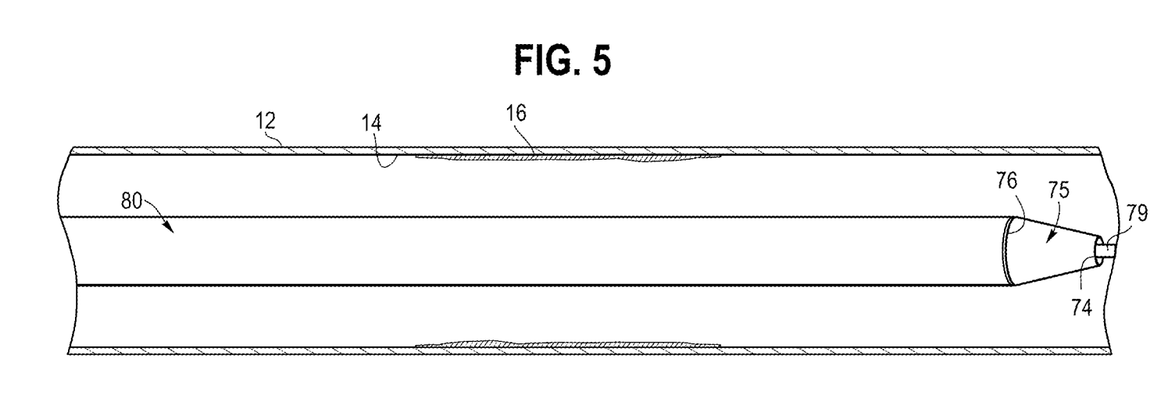
FIGS. 5-8 are side views depicting exemplary methods steps for using the system of FIG. 4 inside a vessel, where a cross-section of the vessel is depicted.

In a first step, as shown in FIG. 5, the system 10' is delivered into the vessel 12 with the stent 20' in the contracted delivery state shown in FIG. 3B. In this state, the sheath 80 may be disposed over both the 20' and the core assembly 60 such the that sheath 80 distally abuts the proximal end 76 of the atraumatic tip 75, thereby providing a substantially flush exterior surface to the overall system 10 suitable for percutaneous delivery. Further, at this time, the coiled portion 42 of the coupling assembly 40 may be selectively engaged to the retaining portion 52, thereby effectively securing the stent 20' to the core assembly 60. Optionally, one or more radiopaque markers may be disposed on the stent and/or the core assembly 60 to facilitate placement of the stent 20' at a desired location within the vessel 12. In this example, a guidewire 79 has been advanced into the vessel 12, and the system is advanced over the guidewire 79 via a lumen of the core assembly 60, until the stent 20' is positioned adjacent to an exemplary medical condition 16 within the vessel 12.

Figure 12:
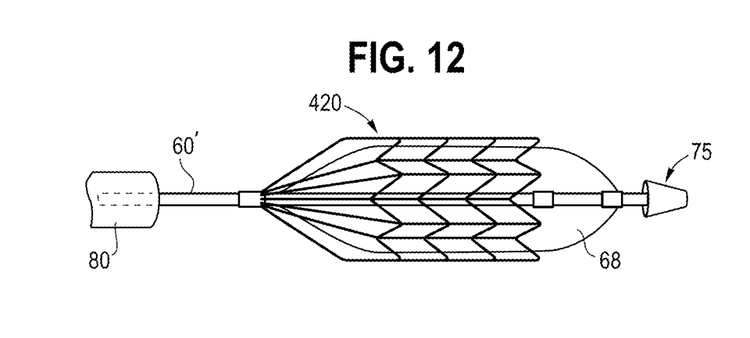
FIG. 12 is a side view of a balloon used to expand a stent in accordance with an alternative embodiment.

Referring to FIG. 6, in a next step, the sheath 80 may be retracted in a proximal direction to expose the stent 20'. At this time, the stent 20' may be deployed radially outward to engage the wall 14 of the vessel 12, and in this example may engage the medical condition 16. The outward deployment may be achieved by self-expansion of the material of the stent 20', as explained in detail above, or via a balloon catheter such as shown in FIG. 12, or by other suitable expansion techniques.

At this time, the stent 20' may deliver the therapeutic agent 70 to the treatment site. There are many factors to determine the duration of the step of delivering the therapeutic agent 70, such as the condition and its severity on the subject, the type of treatment, the type of therapeutic agent 70, and other factors.

In accordance with one aspect, the system 10' can be maintained in the body vessel 12 for a suitable duration of time to deliver the therapeutic agent 70, or the system 10' can be removed and the 20' may be left implanted within the body vessel for a longer period and optionally later removed through an independent procedure, as explained further in FIGS. 7-8 below. Advantageously, due to the design of the stents 20 and 20', and in particular the provision of the series of slots 34 in between adjacent members 32, in conjunction with the tapered regions proximal and distal to the contacting portion 38, blood is allowed to flow in-between the slots 34 and to a location downstream of the stent 20 or 20' even when the stent contacts the vessel wall 14. In this manner, blood perfusion occurs during the duration of the therapeutic agent delivery, which enables the stent 20 or 20' to be in contact with the vessel wall for an increased duration of time with a reduced risk of harm to the patient. This may alleviate pressure on an operator to complete the procedure in a shorter period of time, may enable an increased dosage of the therapeutic agent 70 to be delivered, and provide other advantages.

In the event that an operator wishes to remove the stent 20 or 20' during the current procedure, i.e., while the system 10 or 10' remains in the body and the stent has remained engaged with the core assembly 60 throughout delivery of the therapeutic agent 70, then the stent can be transitioned from the expanded configuration to the compressed configuration. In one embodiment, the sheath 80 can be translated in a distal direction to urge the stent 20 or 20' to the compressed configuration, in which case the proximal taper of the stent 20 or 20' facilitates collapsing of the stent into the distally advancing sheath 80. The stent 20 or 20' can then be removed from the point of treatment and withdrawn from the body vessel 12.

Referring to FIG. 7, after initial engagement of the stent 20' with the wall 14 of the body vessel 12, an operator may determine that it could be beneficial or necessary to disengage the stent 20' from the core assembly 60, and thus leave the stent 20' inside of the body. For example, there may be a dissection, an occlusion, or another condition in the vessel for which the operator determines that disengagement of the stent 20' may be desirable. In this scenario, the operator may rotate the core assembly 60 in a predetermined circumferential direction. At this time, the retaining portion 52 disposed on the core assembly 60 can rotate with respect to the coiled portion 42 extending from the proximal region 26 of the stent 20'. This causes the coiled portion 42 to be translated with respect to the retaining portion 52, thereby causing a disengagement of the stent 20' with respect to the core assembly 60. At this time, the core assembly 60 may be retracted proximally and withdrawn from a patient.

Referring to FIG. 8, if an operator determines that it may be desirable to retrieve the stent 20' after an initial deployment inside the body, the operator may bring in a retrieval system to capture the stent 20'. This may occur in an entirely separate procedure, e.g., days or weeks after initial deployment of the stent 20', or may occur at a later time in the initial procedure. The retrieval system may comprise the core assembly 60 used to initially deploy the stent, or may comprise a different system such as a snare that captures the helical turns 45 and/or proximal region 26 of the stent 20'.

If the retrieval system comprises the core assembly 60, then the operator may distally advance the core assembly 60 into axial engagement with the stent 20', such that the retaining portion 52 is disposed adjacent to the coiled portion 42 of the stent 20'. The core assembly 60 then may be rotated in a predetermined circumferential direction, e.g., opposite to the original direction that caused initial disengagement of the stent 20', in order to re-engage the stent 20' with the core assembly 60 by causing the coiled portion 42 to interlock with the retaining portion 52, as depicted in FIG. 8, The outer sheath 80 may be advanced distally to engage the proximal tapered segment of the stent 20', thereby moving the stent from the expanded configuration of FIG. 2 to the collapsed configuration of FIG. 3B. At this time, the core assembly 60 with the stent 20' secured thereto may be retracted proximally and withdrawn from a patient within the sheath 80.

Advantageously, the systems and methods of the present embodiments allow for to significantly increased flexibility for an operator during a medical procedure. As noted above, due to the design of the stent 20 or 20', and in particular the provision of the series of slots 34 in between adjacent members 32, in conjunction with the tapered regions proximal and distal to the contacting portion 38, the stent 20 or 20' will not block fluid flow for an extended period of time to organs, such as the brain, heart or kidneys, while waiting for the therapy to be complete, e.g., to allow the therapeutic agent 70 to diffuse into the target tissue.

As another advantage, the present systems and methods provide for an option to retain the stent 20 or 20' against the core assembly 60 during the stage of therapeutic agent delivery, and optionally to detach the stent from the core assembly. In contrast, many prior systems simply disengage a stent from a catheter at the time of sheath withdrawal or balloon expansion. In the present embodiments, the stent 20 or 20' remains engaged with the core assembly 60 during expansion, engagement with the vessel wall 12, and delivery of the therapeutic agent 70 for any time period that an operator deems beneficial. Advantageously, the operator is provided with an option, after an initial period of time in which the therapeutic agent 70 is delivered by the stent 20 or 20' engaging the vessel wall 14, of whether to remove the stent 20 or 20', or disengage the stent from the core assembly 60 and thus leave the stent in the vessel.

As yet another advantage, the present systems and methods provide for an option to retrieve the stent 20 or 20' after an initial deployment inside the body. In some situations, an operator may determine that a greater benefit is provided by removing the stent 20 or 20', as opposed to a permanent deployment and exposure within the body. Such removal may be desirable, for example, after the stent 20 or 20' has delivered the therapeutic agent 70 for a predetermined period of time. Since the stent comprises a segment of the coupling assembly 40, e.g., the coiled portion 42 in the example of FIGS. 5-8, then capture of the stent 20 or 20' is facilitated at a later time, should such retrieval be deemed beneficial.

Figure 9A:
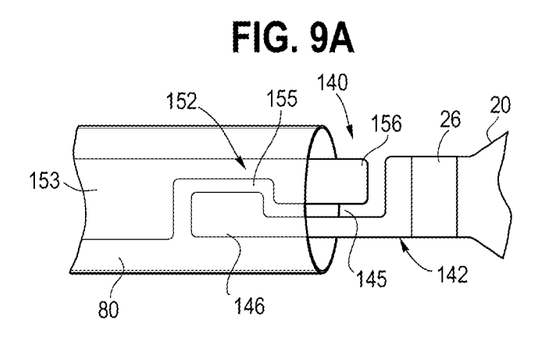
FIGS. 9A-9B are side views depicting an alternative coupling assembly in coupled and uncoupled states, respectively.
Figure 9B:
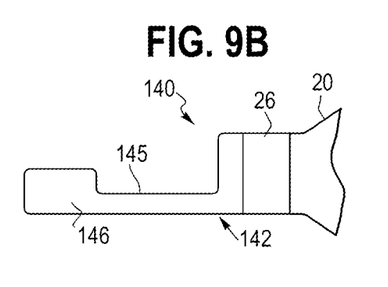
Figure 10A:
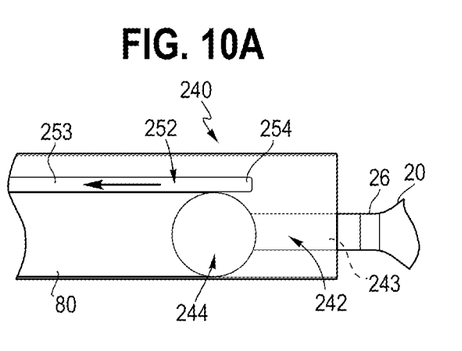
Figure 10B:
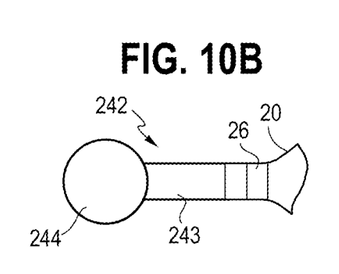
Figure 11A:
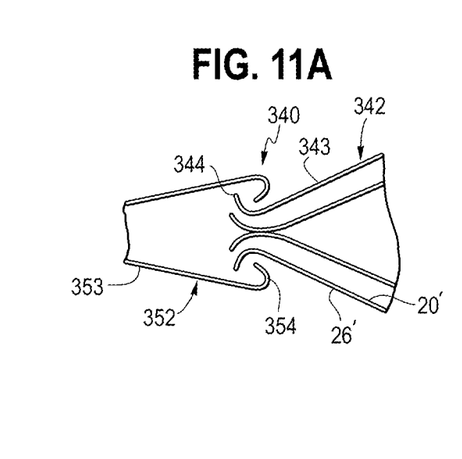
FIGS. 11A-11B are side views depicting yet a further alternative coupling assembly in coupled and uncoupled states, respectively.
Figure 11B:
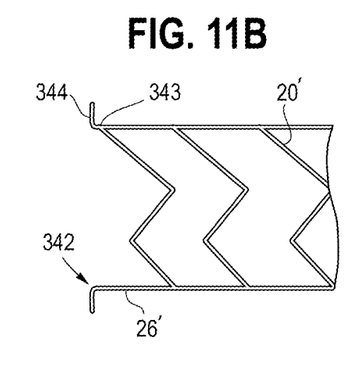

Referring now to FIGS. 9-11, various alternative coupling assemblies are shown, which may be used in lieu of the coupling assembly 40 described in detail above with respect to FIGS. 1-8. In FIGS. 9A-9B, an alternative coupling assembly 140 comprises first and second retainer segments 142 and 152. The first retainer segment 142 is secured or integrally formed to extend from the proximal region 26 of the stent 20, and comprises a notch 145 and a projection 146. The second retainer segment 152 extends distally from a control member 153, such as a wire or pusher, and comprises a notch 155 and a projection 156. The projection 146 of the first retainer segment 142 is in a nested arrangement with the notch 155 of the second retainer segment 152, and similarly the projection 156 of the second retainer segment 152 is in a nested arrangement with the notch 145 of the first retainer segment 142, when the sheath 80 is disposed over the junction of the coupling assembly 140, as depicted in FIG. 9A. The stent 20 may be engaged with the vessel wall to deliver the therapeutic agent 70 for a predetermined period of time before a decision by the operator is made on whether to disengage the stent 20, as depicted in FIG. 9B, by further retraction of the sheath 80 to expose the junction of the coupling assembly.

In FIGS. 10A-10B, an alternative coupling assembly 240 comprises first and second retainer segments 242 and 252. The first retainer segment 242 is secured or integrally formed to extend from the proximal region 26 of the stent 20, and comprises an elongated member 243 transitioning proximally into a projection 244. The second retainer segment 252 comprises an elongated control member 253, such as a wire or pusher, which has a proximal end (not shown) that can be manipulated by an operator, and a distal end 254 that is disposed adjacent to the projection 244 within the sheath 80 in the delivery state of FIG. 10A. In one example, the control member 253 and the projection 244 may form a friction fit with the interior of the sheath 80. In use, the stent 20 may be engaged with the vessel wall to deliver the therapeutic agent 70 for a predetermined period of time before a decision by the operator is made on whether to disengage the stent 20, as depicted in FIG. 1.0B, by retraction of the control member 253 to cause the projection 244 to detach from the control member 253 and sheath 80.

In FIGS. 11A-11B, an alternative coupling assembly 340 comprises first and second retainer segments 342 and 352. The first retainer segment 342 is secured or integrally formed to extend from a proximal region 26' of an alternative stent 20', and comprises at least one elongated member 343 transitioning proximally into a hook 344. The second retainer segment 352 comprises an elongated member 353 transitioning distally into a hook 354, where the hooks 344 and 354 are engaged with one another in the delivery state of FIG. 11A. In use, the stent 20' may be engaged with the vessel wall to deliver the therapeutic agent 70 for a predetermined period of time before a decision by the operator is made on whether to disengage the stent 20', as depicted in FIG. 11B. The disengagement may occur by a mechanism causing expansion of the distal end of the elongated member 353 and the hook 354, at which time the elongated member 343 and hook 344 of the first retainer segment 342 may self-expand outward into engagement with a vessel wall.

In other embodiments, still further coupling assemblies may be provided, while achieving similar goals as coupling assemblies 40, 140, 240 and 340 as described herein. For example, a magnetic coupling mechanism may be employed to selectively detach the stent 20 from the core assembly 60, or an electrical coupling may be employed whereby a current provided causes a detachment of a proximal end of the stent, as will be appreciated by those skilled in the art.

Referring now to FIG. 12, an alternative stent 420 may be expanded by a balloon 68 carried by an alternative core assembly 60'. The core assembly 60' may comprise an inflation lumen (not shown) that delivers fluid to selectively inflate the balloon 68. In this embodiment, drug transfer and stent apposition may be enhanced by the balloon 68. Other features of the system of FIG. 12, and methods of use, are generally similar to the embodiment of FIGS. 1-8.

Figure 13:
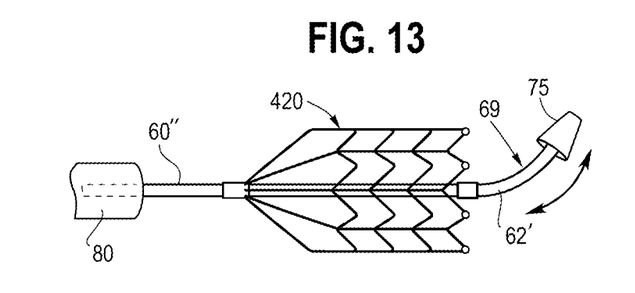
FIG. 13 is a side view of a biased core assembly in accordance with an alternative embodiment.

Referring now to FIG. 13, an alternative core assembly 60" may comprise a biased deflection 69 at its distal region 62. The biased deflection 69 may occur in a delivery state, i.e., when the sheath 80 is disposed over all of the components and abuts the atraumatic tip 75, and also may occur in a deployment state as depicted in FIG. 13. The biased deflection 69 may cause the atraumatic tip 75 to be disposed at an angle between about 5 and 45 degrees relative to a main longitudinal axis, and in this embodiment preferably about 30 degrees. The biased deflection 69 may provide the advantage of improved steerability and trackability of the system.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system for treating a medical condition, the system comprising:
   a stent having proximal and distal regions, and further having a delivery state and an expanded state;
   a therapeutic agent disposed on a segment of the stent;
   a core assembly having proximal and distal regions, wherein the stent is disposed around an exterior surface of the core assembly in the delivery state; and
   a coupling assembly that releasably secures the proximal region of the stent to the exterior surface of the core assembly,
   wherein the coupling assembly secures the stent to the core assembly for a predetermined period while the stent is in the expanded state and during release of the therapeutic agent at a target site, and
   wherein the coupling assembly further enables the stent to be disengaged from the core assembly and deployed in a bodily passageway,
   wherein the coupling assembly comprises a coiled portion extending from the proximal region of the stent, and further comprises a retaining portion disposed on the core assembly, wherein the coiled portion selectively interlocks with the retaining portion,
   wherein the coiled portion has a proximal and distal end, and a plurality of helical turns disposed between the proximal and distal ends, and the plurality of helical turns are in a zone of the selective interlock.

2. The system of claim 1, wherein the stent comprises a proximal taper, a distal taper, and a central region extending therebetween, and further comprises a plurality of members extending axially with a plurality of slots disposed between the plurality of members, wherein the plurality of slots permit perfusion distal to a treatment site when the stent is in the expanded state.

3. The system of claim 1, wherein the coupling assembly further enables recapture of the stent after deployment inside of the bodily passageway.

4. The system of claim 1, wherein the coupling assembly is integrally formed with the proximal region of the stent.

5. The system of claim 1, wherein the core assembly comprises a guidewire lumen.

6. The system of claim 1, wherein the stent comprises a self-expanding material.

7. The system of claim 1, further comprising a balloon coupled to the exterior surface of the core assembly that permits expansion of the stent from the delivery state to the expanded state.

8. A method for treating a medical condition, the method comprising:
providing a stent having proximal and distal regions, and further having a delivery state and an expanded state, wherein a therapeutic agent is disposed on a segment of the stent;
delivering the stent to a target site while disposed around an exterior surface of a core assembly, where a coupling assembly releasably secures the proximal region of the stent to the exterior surface of the core assembly during delivery;
expanding the stent to the expanded state, wherein the coupling assembly secures the stent to the core assembly for a predetermined period while the stent is in the expanded state and during release of the therapeutic agent at a target site, and
actuating the coupling assembly to fully disengage the stent from the core assembly to deploy the stent in a bodily passageway; and
using the coupling assembly to recapture the stent after deployment inside of the bodily passageway.

9. The method of claim 8, wherein the stent comprises a proximal taper, a distal taper, and a central region extending therebetween, and further comprises a plurality of members extending axially with a plurality of slots disposed between the plurality of members, wherein the plurality of slots permit perfusion distal to a treatment site when the stent is in the expanded state.

10. The method of claim 8, where the coupling assembly comprises a coiled portion extending from the proximal region of the stent, and further comprises a retaining portion disposed on the core assembly, wherein the coiled portion selectively interlocks with the retaining portion.

11. A system for treating a medical condition, the system comprising:
an expandable structure having proximal and distal regions, a central region disposed therebetween, and further having a delivery state and an expanded state;
a core assembly having proximal and distal regions, wherein the expandable structure is disposed around an exterior surface of the core assembly in the delivery state; and
a coupling assembly that releasably secures the proximal region of the expandable structure to the exterior surface of the core assembly,
wherein the coupling assembly further enables the expandable structure to be disengaged from the core assembly and deployed in a bodily passageway,
wherein the coupling assembly comprises a coiled portion extending from the proximal region of the expandable structure, and further comprises a retaining portion disposed on the core assembly, wherein the coiled portion selectively interlocks with the retaining portion,
wherein the expandable structure further comprises a proximal taper disposed distal to the coiled portion, wherein the proximal taper transitions to the central region, and wherein the distal region of the expandable structure is flared and comprises a larger outer diameter in the expanded state compared to the proximal region,
wherein the central region of the expandable structure comprises a plurality of axially-extending members, wherein each of the axially-extending members comprises proximal and distal ends, and each of the proximal ends of the axially-extending members are disposed closer to the coupling assembly relative to a respective distal end of the axially-extending members, and wherein the plurality of axially-extending members are separated by a plurality of slots that permit perfusion distal to a treatment site when the expandable structure is in the expanded state.

12. The system of claim 11, wherein a therapeutic agent is disposed on a segment of the expandable structure, and wherein the coupling assembly secures the expandable structure to the core assembly for a predetermined period while the expandable structure is in the expanded state and during release of the therapeutic agent at a target site.

13. The system of claim 11, wherein the expandable structure is a stent.

14. The system of claim 11, wherein the coiled portion has a proximal and distal end, and a plurality of helical turns disposed between the proximal and distal ends, and the plurality of helical turns are in a zone of the selective interlock.

15. The system of claim 11, wherein the coupling assembly further enables recapture of the expandable structure after deployment inside of the bodily passageway.

16. The system of claim 11, wherein the coiled portion is integrally formed with the proximal region of the stent.

17. The system of claim 11, wherein the core assembly comprises a guidewire lumen.

18. The system of claim 11, wherein the expandable structure comprises a self-expanding material.

19. The system of claim 11, further comprising a balloon coupled to the exterior surface of the core assembly that permits expansion of the expandable structure from the delivery state to the expanded state.

* * * * *